United States Patent [19]

Chauvette

[11] 4,060,688
[45] Nov. 29, 1977

[54] CEPHALOSPORIN INTERMEDIATES
[75] Inventor: Robert R. Chauvette, Indianapolis, Ind.
[73] Assignee: Eli Lilly and Company, Indianapolis, Ind.
[21] Appl. No.: 584,548
[22] Filed: June 6, 1975

Related U.S. Application Data
[63] Continuation-in-part of Ser. No. 310,191, Nov. 28, 1972, Pat. No. 3,917,587.

[51] Int. Cl.² .............................................. C07D 501/22
[52] U.S. Cl. ........................................ 544/30; 544/16; 424/246
[58] Field of Search ................................... 260/243 C

[56] References Cited
U.S. PATENT DOCUMENTS

| | | | |
|---|---|---|---|
| 3,775,408 | 11/1973 | Ochiai et al. | 260/243 C |
| 3,792,995 | 2/1974 | Ochiai et al. | 260/243 C |
| 3,883,518 | 5/1975 | Ponticello et al. | 260/243 C |
| 3,917,587 | 11/1975 | Chauvette | 260/243 C |
| 3,932,393 | 1/1976 | Chauvette | 260/243 C |

Primary Examiner—Nicholas S. Rizzo
Attorney, Agent, or Firm—William B. Scanlon; Everet F. Smith

[57] ABSTRACT

3-Exomethylenecepham and 3-hydroxy-3-cephem sulfoxides represented by the formulas

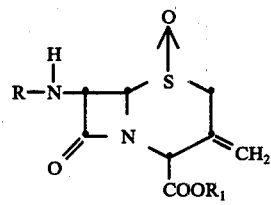

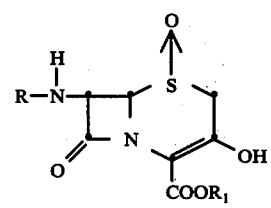

wherein R is an acyl group derived from a carboxylic acid and $R_1$ is a carboxylic acid protecting group, are useful intermediates in the synthesis of 3-alkoxy-3-cephem, 3-chloro-3-cephem and 3-methyl-3-cephem antibiotic compounds.

5 Claims, No Drawings

CEPHALOSPORIN INTERMEDIATES

CROSS REFERENCE TO RELATED APPLICATIONS

This application is a continuation-in-part of copending application Ser. No. 310,191 filed Nov. 28, 1972 now U.S. Pat. No. 3,917,587 issued Nov. 4, 1975.

BACKGROUND OF THE INVENTION

In U.S. Pat. No. 3,275,626 issued Sept. 27, 1966 Morin and Jackson disclose the formation of cephalosporin compounds having an exocyclic double bond in the 3-position of the cepham ring system. Subsequently, in my copending application Ser. No. 118,941 filed Feb. 25, 1971 now U.S. Pat. No. 3,932,393 issued Jan. 13, 1976 the preparation of 3-exomethylenecepham compounds with 3thio-substituted-methylcephalosporins is described. For example, cephalosporins substituted on the 3'-methyl group with tioureas (isothiouronium salts) are reduced under hydrogen in the presence of Raney nickel or with zinc and formic acid in the presence of dimethylformamide to provide the 3-exomethylenecepham compounds.

More recently in my copending application Ser. No. 310,191 filed on Nov. 28, 1972 now U.S. Pat. No. 3,917,587 issued Nov. 4, 1974 the oxidation of 3-exomethylenecepham esters with ozone is described. The predominant product of the ozonolysis described therein is the 3-hydroxy-3-cephem ester which is reacted with a diazoalkene to provide the corresponding ester of a 3-alkoxy-3-cephem. Removal of the ester group provides the alkoxylated antibiotic compound. For example, 7-phenoxyacetamido-3-hydroxy-3-cephem-4-carboxylic acid p-nitrobenzyl ester, obtained by the ozonolysis of the corresponding 3-exomethylene compound, is reacted with diazomethane to form p-nitrobenzyl 7-phenoxyacetamido-3-methoxy-3-cephem4-carboxylate. The p-nitrobenzyl ester group is removed by catalytic hydrogenolysis in the presence of 5% palladium on carbon catalyst to provide the free carboxylic acid antibiotic compound. In the same application Ser. No. 310,191, the formation of 3-exomethylenecepham-4-carboxylic ester sulfoxides and 3-hydroxy-3-cephem-4-carboxylic acid ester sulfoxides are disclosed as side products of the ozonolysis reaction of 3-exomethylenecepham esters.

This invention relates to 7-acylamido-3-exomethylenecepham-4-carboxylic acid and ester sulfoxides and 7-acylamido3-hydroxy-3-cephem-4-carboxylic acid ester sulfoxides.

DETAILED DESCRIPTION

The cephalosporin sulfoxide intermediates of this invention are represented by the following structural formula

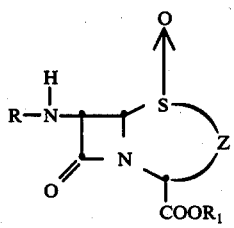

wherein R is hydrogen, $C_2$-$C_7$ alkanoyl, cyanoacetyl, haloacetyl, 5'-protected-amino-5'-carboxyvaleryl, or an acyl group of the formula

wherein R' is phenyl, or phenyl substituted by halogen, hydroxy, nitro, amino, cyano, $C_1$-$C_4$ lower alkyl, $C_1$-$C_4$ lower alkoxy, hydroxymethyl, aminomethyl, carboxy, or carboxymethyl; or an acyl group of the formula

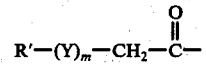

wherein R' is as defined above, Y is O or S, and $m$ is 0 or 1;
or a substituted acyl group of the formula

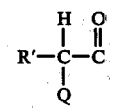

wherein R' is as defined above and Q is hydroxy protected hydroxy, amino or protected amino; or R is an acyl group of the formula

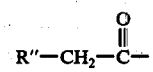

wherein R" is thienyl or furyl;
wherein $R_1$ is a carboxylic acid protecting ester forming group;
and wherein Z is a

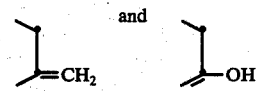

In the above formula the term "$C_2$-$C_7$ alkanoyl" refers to acetyl, propionyl, n-butyryl, isobutyryl, valeryl, caproyl, and heptoyl. "Haloacetyl" refers to chloroacetyl and bromoacetyl. The term "5'-protected-amino-5'-carboxyvaleryl" refers to the acyl groups of the formula

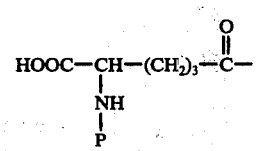

wherein P represents one of the many commonly employed amino-protecting groups. Representative of these groups are those which with the amino nitrogen form urethanes for example, the alkyloxycarbonyl groups such as t-butyloxycarbonyl, the haloalkyloxycarbonyl groups such as 2,2,2-trichloroethoxycarbonyl, the arylakyloxycarbonyl groups such as benzyloxycarbonyl and a substituted benzyloxycarbonyl group such as p-nitrobenzyloxycarbony; the protecting groups which with the amino group form enamines such as those formed with ethyl acetoacetate and acetyl acetone; the alkenyl, haloalkenyl, and acyl protecting groups such as acetyl, propionyl, chloroacetyl, dichloroacetyl, benzoyl, substituted benzoyl groups for example, 2,4-dichlorobenzoyl, and 4-nitrobenzoyl; or P represents the diarylmethyl and triarylmethyl protecting groups such as the benzhydryl and trityl groups; or R can be the o-nitrophenylsulfenyl group.

When in the foregoing formula R' is a substituted phenyl group as defined therein R' can be a mono or disubstituted halophenyl group such as 4-chlorophenyl, 2,6-dichlorophenyl, 2,4-dichlorophenyl, 3,4-dichlorophenyl, 3-chlorophenyl, 3-bromophenyl, 3,4-dibromophenyl, 4-bromophenyl, 4-fluorophenyl, 2-fluorophenyl and the like; a mono or dihydroxyphenyl group such as 4-hydroxyphenyl, 3-hydroxyphenyl, 2,4-dihydroxyphenyl and the like; a mono-nitrophenyl group such as 3- or 4-nitrophenyl; an aminophenyl group such as 4-aminophenyl, 3-aminophenyl, or 2-aminophenyl; a cyanophenyl group, for example, 4-cyanophenyl; a mono or disubstituted lower alkyl phenyl group such as methylphenyl for example 4-methylphenyl, 2,4-dimethylphenyl, 2-methylphenyl, or a higher alkylphenyl group such as for example 4-isopropyl-phenyl, 4-ethylphenyl, 3-n-propylphenyl and the like; a mono or disubstituted lower alkoxyphenyl group for example 4-methoxyphenyl, 3-ethoxyphenyl, 2,6-dimethoxyphenyl, 4-isopropoxyphenyl, 4-t-butoxyphenyl, 3-ethoxy-4-methoxyphenyl and the like; or R can represent an aminomethylphenyl group such as the 3- or 4-aminomethylphenyl group; a carboxyphenyl group such as 3- or 4-carboxyphenyl; or R represents a carboxymethylphenyl group such as the 3- or 4-carboxymethylphenyl. Also, R' represents disubstituted phenyl groups wherein the substituents can be different, for example 3-methyl-4-hydroxyphenyl, 3-chloro-4-hydroxyphenyl, 2-methoxy-4-bromophenyl, 4-ethyl-2-hydroxyphenyl, 2-hydroxy-4-carboxyphenyl and like disubstituted phenyl groups.

When in the above formula Q represents a protected hydroxy group, Q represents such groups as the formyloxy group, the chloroacetoxy group, the benzhydroyloxy group, the trityloxy group, the benzyloxy group, the p-nitrobenzyloxy group, a trialkylsilyloxy group such as trimethylsilyloxy, or the protected hydroxy group formed with methyvinyl ether for example Q can represent the 1-methoxyethoxy group.

When in the foregoing formula, Q represents a protected amino group such groups can be represented by the term

wherein P has the previously defined meanings for conventional amino-protecting groups. Preferred amino-protecting groups are the t-butyloxycarbony group, the trichloroethoxycarbonyl group, or the enamine formed with ethyl acetoacetate.

Representative of the acyl groups

wherein R' is phenyl or substituted phenyl are benzoyl, 2,6-dimethoxybenzoyl, 4-chlorobenzoyl, 4-methylbenzoyl, 3,4-dichlorobenzoyl, 4-cyanobenzoyl, 3-bromobenzoyl, 3-aminobenzoyl, and 4-nitrobenzoyl.

Illustrative of the acyl groups

when R' is a group of the formula R'—(Y)$_m$—CH$_2$— and m is O, the phenylacetyl, 4-chlorophenylacetyl, 3-hydroxyphenylacetyl, 4-carboxyphenylacetyl, 3-cyanophenylacetyl, 4-aminophenylacetyl, 4-hydroxy3-methylphenylacetyl, 4-bromophenylacetyl, 4-methoxyphenylacetyl, 4ethoxyphenylacetyl, 4-nitrophenylacetyl, 3,4-dimethoxyphenylacetyl, and like acyl groups, and when m is 1 and Y is O, representative acyl groups are phenoxyacetyl, 3-hydroxyphenoxyacetyl, 4-chlorophenoxyacetyl, 3,4-dichlorophenoxyacetyl, 2-chlorophenoxyacetyl, 4-methoxyphenoxyacetyl, 3-aminophenoxyacetyl, 3-aminophenoxyacetyl, 4-carboxymethylphenoxyacetyl, 2-ethoxyphenoxyacetyl, 3,4-dimethylphenoxyacetyl, 4-isopropylphenoxyacetyl, 3-cyanophenoxyacetyl, 3-nitrophenoxyacetyl and like substituted phenoxacetyl groyps and when m is 1 and Y is S, representative thiophenoxyacetyl, 2,6-dichlorothiophenoxyacetyl, 4-chlorothiophenoxyacetyl, 4-cyanothiophenoxyacetyl, 3-bromothiophenoxacetyl, 3-aminothiophenoxyacetyl and like acyl groups.

When in the above formula Q is hydroxy and R' is phenyl or substituted phenyl, illustrative of the acyl groups are 4-methoxymandeloyl, 4-hydroxymandeloyl, 3,4-dichloromandeloyl, 3-bromomandeloyl, 3-hydroxymandeloyl, 4-aminomandeloyl, 4-fluoromandeloyl, 4-carboxymandeloyl, 4-carboxymethylmandeloyl, 4-aminomethylmandeloyl, and like acyl groups.

Illustrative of the cephalosporin sulfoxide acids and esters defined above are the unacylated 3-exomethylenecepham-4-carboxylic acid sulfoxides and the esters thereof for example:

7-amino-3-exomethylenecepham-4-carboxylic acid sulfoxide, p-nitrobenzyl 7-amino-3-exomethylenecepham-4-carboxylate sulfoxide, p-methoxybenzyl 7-amino-3-exomethylenecepham-4-carboxylate sulfoxide, 2,2,2-trichloroethyl 7-amino-3-exomethylenecepham-4-carboxylate sulfoxide, diphenylmethyl 7-amino-3-exomethylenecepham-4-carboxylate sulfoxide, benzyl 7-amino-3-exomethylenecepham-4-carboxylate sulfoxide, and the salts thereof formed with mineral acids and sulfonic acids for example the hydrochloride, hydrobromide, sulfate, phosphate, benzenesulfonate, p-toluenesulfonate, naphthalenesulfonate, methanesulfonate and ethanesulfonate.

Representative 7-acylamido-3-exomethylenecepham acid and ester sulfoxides are the following.

p-nitrobenzyl 7-acetamido-3-exomethylenecepham-4-carboxylate sulfoxide, diphenylmethyl 7-chloroacetamido-3-exomethylene-cepham-4-carboxylate sulfoxide, p-methoxybenzyl 7-cyanoacetamido-3-exomethylene-cepham-4-carboxylate sulfoxide, benzyl 7-benzamido-3-exomethylenecepham-4-carboxylate sulfoxide, 7-phenylacetamido-3-exomethylenecepham-4-carboxylic acid sulfoxide, p-nitrobenzyl 7-phenylacetamido-3-exomethylene-cepham-4-carboxylate sulfoxide, p-methoxybenzyl 7-(4-nitrophenylacetamido)-3-exomethylenecepham-4-carboxylate sulfoxide, 7-phenoxyacetamido-3-exomethylenecepham-4-carboxylic acid sulfoxide, p-nitrobenzyl 7-phenoxyacetamido-3-exomethylenecepham-4-carboxylate sulfoxide, 2,2,2-trichloroethyl 7-phenoxyacetamido-3-exomethylenecepham-4-carboxylate sulfoxide, diphenylmethyl 7-phenoxyacetamido-3-exomethylene-cepham-4-crboxylate sulfoxide, p-methoxybenzyl 7-(2,6-dimethoxybenzamido)-3-exomethylenecepham-4-carboxylate sulfoxide, diphenylmethyl 7-(D-mandelamido)-3-exomethylenecepham-4-carboxylate sulfoxide, p-nitrobenzyl 7-(D-2-formyloxy-2-phenylacetamido)-3-exomethylenecepham-4-carboxylate sulfoxide, p-nitrobenzyl 7-(D-2-t-butyloxy-2-phenylacetamido)-3-exomethylenecepham-4-carboxylate sulfoxide, p-methoxybenzyl 7-[2-(2-thienyl)acetamido]-3-exomethylenecepham-4-carboxylate sulfoxide, p-nitrobenzyl 7-[2-(2-thienyl)acetamido]-3-exomethylenecepham-4-carboxylate sulfoxide, diphenylmethyl 7-[2-(2-furyl)acetamido]-3-exomethylenecepham-4-carboxylate sulfoxide, 2,2,2-trichloroethyl 7-[2-(2-thienyl)acetamido]-3-exomethylenecepham-4-carboxylate sulfoxide, p-nitrobenzyl 7-(2-t-butyloxycarbamido-2-phenylacetamido)-3-exomethylenecepham-4-carboxylate and 2,2,2-trichloroethyl 7-(D-phenylglycylamido)-3-exomethylenecepham-4-carboxylate hydrochloride.

Illustrative 3-hydroxy-3-cephem ester sulfoxides defined above are 4-nitrobenzyl 7-amino-3-hydroxy-3-cephem-4-carboxylate sulfoxide, 4-nitrobenzyl 7-phenoxyacetamdio-3-hydroxy-3-cephem-4-carboxylate sulfoxide, diphenylmethyl 7-phenylacetamido-3-hydroxy-3-cephem-4-carboxylate sulfoxide, 2,2,2-trichloroethyl 7-acetamido-3-hydroxy-3-cephem-4-carboxylate sulfoxide, 4-methoxybenzyl 7-[2-(2-thienyl)-acetamido]-3-hydroxy-3-cephem-4-carboxylate sulfoxide, benzyl 7-benzamido-3-hydroxy-3-cephem-4-carboxylate sulfoxide, 4-nitrobenzyl 7-(2-t-butyloxycarbamido-2-phenylacetamido)-3-hydroxy-3-cephem-4-carboxylate sulfoxide, 4-nitrobenzyl 7-(D-mandelamido)-3-hydroxy-3-cephem-4-carboxylate sulfoxide, and diphenylmethyl 7-(2-formyloxy-2-phenylacetamido)-3-hydroxy-3-cephem-4-carboxylate sulfoxide.

A preferred group of sulfoxides of this invention are the compounds represented by the foregoing structural formula wherein R is hydrogen, $C_2$-$C_7$ alkanoyl, benzoyl, phenoxyacetyl, phenylacetyl, mandeloyl, or mandeloyl wherein the hydroxy group is protected, thienylacetyl or furylacetyl.

The 3-exomethylenecepham and 3-hydroxy-3-cephem ester sulfoxides of this invention are prepared by three methods. In the first of these methods a 7-acylamido-3-exomethylenecepham-4-carboxylic acid ester or a 7-amino-3-exomethylenecepham-4-carboxylic acid ester in the form of an amine salt for example the hydrochloride salt, is reacted with ozone in an inert solvent at sub-zero temperatures to provide as the predominant product the corresponding 7-acylamido or 7-amino-3-hydroxy-3-cephem ester and the side products, the corresponding 3-hydroxy-3-cephem ester sulfoxide and the 3-exomethylenecepham ester sulfoxide. The ozonolysis method is disclosed in my copending application Ser. No. 310,191 filed on Nov. 28, 1972 now U.S. Pat. No. 3,917,587 issued Nov. 4, 1975 and is illustrated by the following reaction scheme 1.

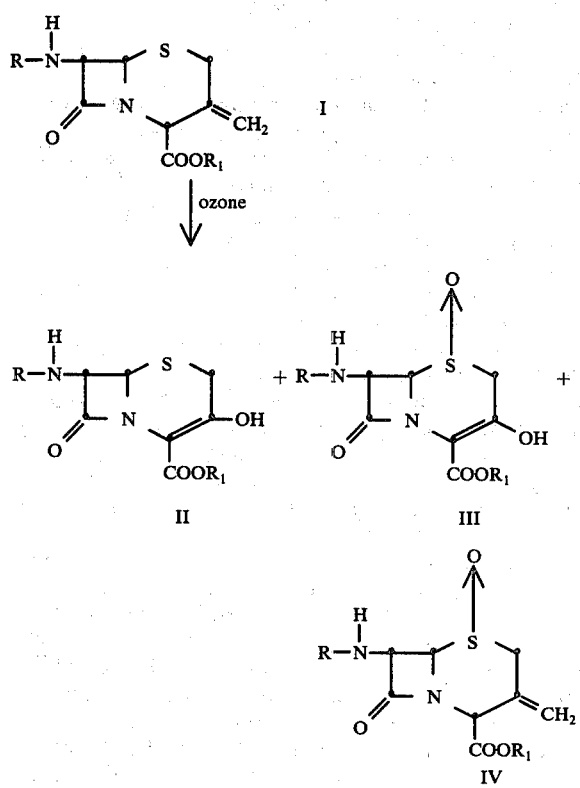

As disclosed in my copending application the ozonolysis of the 3-exomethylenecepham ester is carried out by passing ozone through a solution of the ester in an inert solvent at a temperature between about −80° and 0° C. The exomethylene double bond of the 3-exomethylenecepham ester reacts with ozone to form in situ an intermediate ozonide which, following decomposition forms the predominant product the 3-hydroxy-3-cephem ester represented by the formula II in the above reaction scheme. Also formed in the oxidation of the 3-exomethylenecepham ester are the sulfoxide side products, the 3-exomethylenecepham sulfoxide ester and the 3-hydroxy-3-cephem sulfoxide ester, structurally depicted by formulas III and IV in the above reaction scheme.

Although the sulfoxide ozonolysis products occur as minor side products in the reaction mixture they cay be separated from the predominant product, the 3-hydroxy-3-cephem ester, and from each other by chromatography over silica gel.

The ozone employed in the ozonolysis is prepared by means of an ozone generator of the type commonly used in synthetic and analytical work which produces ozone by the action of an electric discharge on a stream of oxygen or air. The ozone is generated in a stream of oxygen which is then passed into the reaction vessel. The percentage of ozone contained in the oxygen stream can be varied, for example by varying the rate of flow of oxygen through the ozonizer as well as by varying the intensity of the electric discharge.

Inert solvents which can be used in the ozonolysis of the 3-exomethylenecepham esters are those solvents in which the cepham esters are at least partially soluble and which are unreactive with ozone under the described conditions. Commonly used organic solvents such as methanol, ethanol, ethyl acetate, methyl acetate, and methylene chloride are satisfactory.

The ozonolysis is preferably carried out at a temperature between about −80° and −50° C.

The sulfoxide ester side products of the reaction, particularly the 3-hydroxy-3-cephem sulfoxide ester are formed in greater amounts when the ozonolysis reaction is carried out by employing a large excess of ozone.

The time over which the ozonolysis is carried out on a given scale reaction can be determined by measuring iodometrically the amount of ozone in the gas stream coming from the ozonizer with time. This can be determined by titrating with sodium thiosulfate the amount of iodine liberated from a standard solution of potassium iodode by the ozone stream.

Alternatively, the ozonolysis reaction can be followed chromatographically. For example, a small aliquot of the reaction mixture is withdrawn, the ozonide decomposed, and the amounts of unreacted starting material and reaction products present in the sample is assessed by a comparison of the thin layer chromatogram with that of a known amount of starting material and reaction products.

After passage of the ozone through the reaction mixture is discontinued any excess ozone present in the reaction mixture is desirably purged by bubbling nitrogen, oxygen, or an inert gas through the mixture. Following the removal of any excess ozone the ozonide in the cold reaction mixture is decomposed by adding a mild reducing agent such as sodium bisulfite, sulfur dioxide, or trimethyl phosphite. Preferred mild reducing agents for decomposing the intermediate ozonide are gaseous sulfur dioxide and trimethyl phosphite. These reagents are preferred in that they are easily disposed of during the workup of the reaction products and consequently they do not complicate the recovery of the reaction products.

As mentioned above the ozonolysis reaction products, represented by the structural formulas II, III, and IV in the above reaction scheme, are recovered from the reaction mixture and are separated by chromatography over silica gel. Following the decomposition of the ozonide the reaction mixture is allowed to warm to room temperature and is thereafter evaporated under reduced pressure to provide a reaction product mixture as a dry residue. The residue is dissolved in a minimal amount of an organic solvent for example ethyl acetate and the solution is poured onto a column packed with silica gel. The column is initially eluted with an organic solvent mixture of relatively low polarity to obtain off the column the predominant product, the 3-hydroxy-3-cephem ester. Thereafter the polarity of the eluting solvent mixture is increased to elute successively the 3-exomethylenecepham sulfoxide ester and the 3-hydroxy-3-cephem sulfoxide exter. The sulfoxide ester products of the ozonolysis are considerably more polar substances than is the predominant product, the 3-hydroxy-3-cephem ester. Accordingly the pedominant product is eluted initially by employing a relatively nonpolar solvent mixture. The sulfoxide ester products can then be eluted off the column separately by increasing the polarity of the eluting solvent mixture. A useful solvent mixture which can be employed during the initial elution of the column is benzene:ethyl acetate, 10:1, v:v. After the predominant product has been eluted the polarity of the mixture is increased by increasing the proportion of ethyl acetate. For example a 1:1, v:v mixture of benzene-ethyl acetate can then be used to elute the sulfoxide esters. Other useful solvent mixtures are benzene:isopropyl acetate, 1:1 and ethyl acetate:acetic acid, 20:1.

The course of the chromatography can be followed by periodically collecting a small sample of eluate and assaying the eluate by thin layer chromatography or paper chromatography comparison with authentic materials.

In an example of the preparation of a preferred 3-exomethylenecepham sulfoxide ester and a preferred 3-hydroxy-3-cephem sulfoxide ester by the ozonolysis process, 4-nitrobenzyl 7-phenoxyacetamido-3-exomethylenecepham-4-carboxylate is dissolved in ethyl acetate and the solution is cooled to about −78° C. by means of a dry ice-acetone bath. Excess ozone is then passed through the cold reaction mixture and thereafter the ozonide formed is decomposed by adding excess sodium bisulfite. The reaction mixture is allowed to stir at 0° C. for about 30 minutes. The organic layer is separated from the excess insoluble sodium bisulfite, is washed with water, dried and then evaporated under reduced pressure. The residue is then dissolved in the minimum amount of ethyl acetate and the solution applied to a column packed with silica gel. The column is eluted with benzene:ethyl acetate, 10:1, v:v and multiple fractions of eluate are collected. When all of the 3-hydroxy-3-cephem ester has been eluted from the column, the column is then further eluted with a 1:1 mixture of benzene and ethyl acetate. The next product eluted from the column is 4-nitrobenzyl 7-phenoxyacetamido-3-exomethylenecepham-4-carboxylate sulfoxide and finally the most polar of the products, 4-nitrobenzyl 7-phenoxyacetamido-3-hydroxy-3-cephem-4-carboxylate sulfoxide is eluted. The middle fractions containing the 3-exomethylenecepham sulfoxide ester are combined and evaporated to yield the 4-nitrobenzyl 7-phenoxyacetamido-3-exomethylene cepham-4-carboxylate sulfoxide. The fractions containing the 3-hydroxy-3-cephem sulfoxide ester are combined and evaporated to dryness to afford the 4 nitrobenzyl 7-phenoxyacetamido-3-hydroxy-3-cephem-4-carboxylate sulfoxide.

In a further example of the preparation of a preferred compound of the invention, 4-nitrobenzyl 7-amino-3-exomethylenecepham-4-carboxylate hydrochloride is dissolved in methanol and ozone is bubbled through the solution at a temperature of about −78° C. Excess ozone is purged from the reaction mixture with dry nitrogen and the ozonide present is decomposed by bubbling sulphur dioxide through the cold mixture. The reaction mixture is evaporated to dryness and the residue dissolved in ethyl acetate. The ethyl acetate solution is treated with triethylamine to liberate the free 7-amino form of the ozonization products. The ethyl acetate solution is then washed with water and dried over sodium sulfate. The dried ethyl acetate solution is then chromatographed over silica gel as previously described to provide 4-nitrobenzyl 7-amino-3-exomethylenecepham-4-carboxylate sulfoxide and 4-nitrobenzyl 7-amino-3-hydroxy-3-cephem-4-carboxylate sulfoxide along with the predominant product, the 4-nitrobenzyl 7-amino-3-hydroxy-3-cephem-4-carboxylate.

The starting materials employed in the ozonolysis method for preparing the compounds of this invention, namely the esters of 7-acylamido and 7-amino-3-exomethylenecepham-4-carboxylic acids, are obtained as described in my copending application Ser. No. 118,941 filed on Feb. 25, 1971 now U.S. Pat. No. 3,932,393 issued Jan. 13, 1976. The methods for the preparation of these exomethylenecepham esters is incorporated herein by reference.

According to a second method for the preparation of the compounds described herein, a 3exomethylenecepham acid or ester, or an ester of a 3-hydroxy-3-cephem is reacted in an ineet solvent with sodium meta-periodate or with an organic peracid for example, peracetic acid, perbenzoic acid, perphthalic acid, and preferably m-chloroperbenzoic acid. This method is illustrated in the following reaction scheme 2.

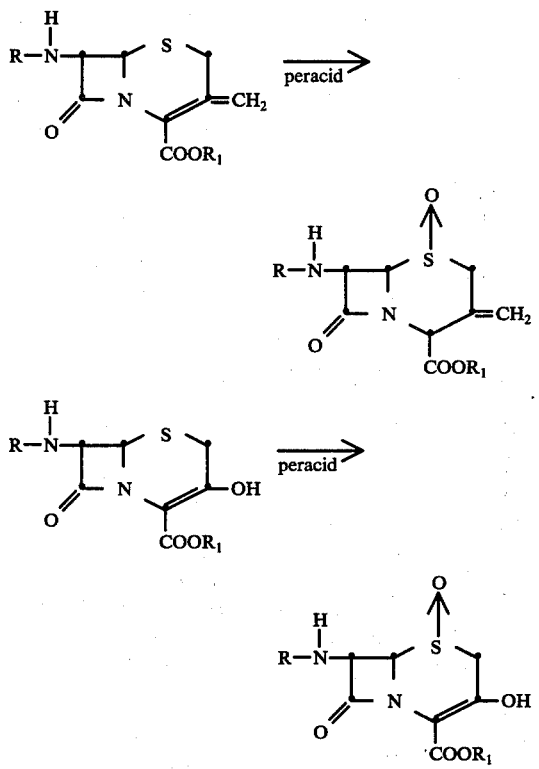

The 3-hydroxy-3-cephem ester designated as II in the above reaction scheme is prepared by the ozonolysis of a 3-exomethylenecepham ester as previously described. The 3-exomethylenecepham acid or ester designated in the above reaction scheme as I is the same starting material employed in the ozonolysis method as set forth in reaction scheme I.

The peracid oxidation of I or II is carried out in an inert solvent which may be either an aqueous or nonaqueous solvent such as for example, aqueous acetic acid or methylene chloride at a temperature between about 5° and 25° C. In contrast to the ozonolysis of a 3-exomethylenecepham compound as described above, the peracid oxidation is selective in the formation of the sulfoxide. The 3-exo double bond does not undergo oxidation under the conditions employing a peracid. When a 3-hydroxy-3-cephem compound is employed as the starting material in the peracid oxidation, it is employed in the form of an ester to protect the $C_4$ carboxyl group. The 3-hydroxy-3-cephem esters are stable compounds. However, in the free acid form, they tend to decarboxylate.

The preferred method for the preparation of the 3-exomethylenecepham sulfoxides of this invention comprises the cyclization of an azetidinone sulfinyl chloride by reacting the sulfinyl chloride in an inert organic solvent with a Lewis acid type Friedel-Crafts catalyst. This method is described by S. Kukolja in copending application Ser. No. 536,280 filed Dec. 24, 1974.

The cyclization of an azetidinone sulfinyl chloride with a Friedel-Crafts type catalyst is shown in the following reaction scheme 3.

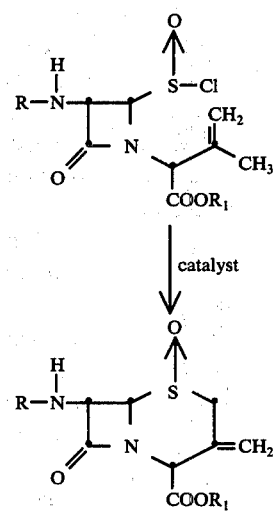

wherein R and $R_1$ are as described in the previous formulas.

The azetidinone sulfinyl chlorides depicted by the structural formula V in the above reaction scheme are formally named as 3-methyl-2-(2-chlorosulfinyl-4-oxo-3-acylamido-1-azetidinyl)-3-butenoic acid esters. These compounds are prepared from the correspondingly substituted penicillin sulfoxide ester by reacting the penicillin ester sulfoxide at elevated temperatures with a positive chlorine reagent preferably an N-chloroimide such as N-chlorosuccinimide. For example, the penicillin sulfoxide ester is reacted with at least about 1.1 equivalents of N-chlorosuccinimide in a dry, inert organic solvent, for example, a chlorinated hydrocarbon such as 1,1,2-trichloroethane or an aromatic hydrocarbon such as toluene, at a temperature between about 70° and 120° C. For example, 4-nitrobenzyl 6-acetamidopenicillanate sulfoxide is dissolved in dry toluene and 1.5 molar equivalents of N-chlorosuccinimide is added to the solution. The reaction mixture is refluxed for between one to two hours and thereafter is allowed to cool to room temperature. The reaction mixture is filtered to remove insolubles and the filtrate is evaporated in vacuo to provide the correspondingly substituted azetidinone sulfinyl chloride, 4-nitrobenzyl 3-methyl-2-(2-chlorosulfinyl-4-oxo-3-acetamido-1-azetidinyl)-3-butenoate.

In a similar fashion, compounds represented by the structural formula V in the above reaction scheme 3 wherein R represents phenylacetyl, phenoxyacetyl, propionyl, and benzoyl and substituted benzoyl and wherein $R_1$ represents a carboxylic acid protecting ester group such as benzyl benzhydryl, substituted benzyl for example, 4-methoxybenzyl, 4-nitrobenzyl, or t-butyl are prepared.

As previously mentioned, the cyclization of an azetidinone sulfinyl chloride is carried with a Friedel-Crafts type catalyst in a dry, inert organic solvent. Lewis acid type catalysts of the Friedel-Crafts type include for example, alluminum chloride, stannic chloride, stannic bromide, zinc chloride, antimony pentafluoride, titanium tetrachloride, zinc bromide, ferric chloride, and zirconium tetrachloride. Preferred among these Friedel-Crafts catalysts are stannic chloride, zinc chloride, zinc bromide, titanium tetrachloride, and zirconium tetrachloride. Stannis chloride is an especially preferred catalyst in the cyclization to form the 3-exomethylene sulfoxide ester.

Inert organic solvents which can be employed are preferably aprotic organic solvents, for example the aromatic hydrocarbons such as benzene, toluene, xylene, nitrobenzene and the like; the halogenated aliphatic hydrocarbons such as chloroform, methylene chloride, and 1,2-dichloroethane.

The cyclization of the azetidinone sulfinyl chloride is preferably carried out at a temperature between about 20° and about 85° C.

The Lewis acid Friedel-Crafts type catalyst such as one of those mentioned above is employed in at least a mole per mole ratio with respect to the sulfinyl chloride. Preferably about 1.1 equivalents of metal halide Lewis acid is used.

The last of the above-described methods for the preparation of 3-exomethylenecepham sulfoxide esters accordingly provides a synthetic route for preparing these compounds with penicillin sulfoxide starting materials. In an example of this overall process, a solution of 4-nitrobenzyl 6-phenoxyacetamidopenicillanate in dry toluene is prepared and 1.1 molar equivalents of N-chlorosuccinimide is added. The solution is refluxed for approximately 90 minutes and then is cooled to about 50° C. The reaction mixture thus obtained contains the azetidinone sulfinyl chloride, namely 4-nitrobenzyl 3-methyl-2-(2-chlorosulfinyl-4-oxo-3-phenoxyacetamido-1-azetidinyl)-3-butenoate, which is not isolated. To the mixture containing the azetidinone sulfinyl chloride is added 1.1 molar equivalents of anhydrous stannic chloride. The mixture thus obtained was stirred at room temperature for about 90 minutes. Water and ethyl acetate are added to the reaction mixture and the organic layer is separated. The organic layer containing the product is washed with dilute acid, aqueous bicarbonate, and finally with brine. The washed organic layer is then dried and evaporated to dryness under vacuum to yield the product, 4-nitrobenzyl 7-phenoxyacetamido-3-exomethylenecepham-4-carboxylate sulfoxide.

By following the same procedures as described in the preceding example, 4-methoxybenzyl 6-phenoxyacetamidopenicillanate sulfoxide is converted via the correspondingly substituted azetidinone sulfinyl chloride to 4-methoxybenzyl 7-phenoxyacetamido-3-exomethylenecepham-4-carboxylate sulfoxide.

Certain of the compounds of this invention are preferred over others for reasons of availability of starting materials, ease of preparation, as well as usefulness in the conversion to other cephalosporin antibiotics. Preferred 3-exomethylenecepham sulfoxide acids and esters are shown in the following Table I.

Table I

3-Exomethylenecepham Sulfoxides

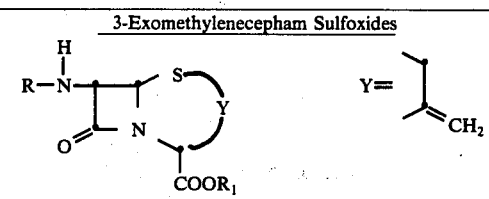

| R | $R_1$ |
|---|---|
| acetyl | H |
| " | 4-nitrobenzyl |
| " | diphenylmethyl |
| " | 2,2,2-trichloroethyl |
| " | 4-methoxybenzyl |
| phenylacetyl | H |
| " | 4-nitrobenzyl |
| " | benzyl |
| " | diphenylmethyl |
| " | 2,2,2-trichloroethyl |
| " | 4-methoxybenzyl |
| phenoxyacetyl | H |
| " | benzyl |
| " | diphenylmethyl |
| " | 4-nitrobenzyl |
| " | 4-methoxybenzyl |
| " | 2,2,2-trichloroethyl |
| " | phenacyl |
| H (7-amino) | H |
| " | 4-nitrobenzyl |
| " | 4-methoxybenzyl |
| " | diphenylmethyl |

Preferred 3-hydroxy-3-cephem sulfoxide esters of this invention are listed in the following Tabel II.

Table II

3-Hydroxy-3-Cephem Sulfoxides

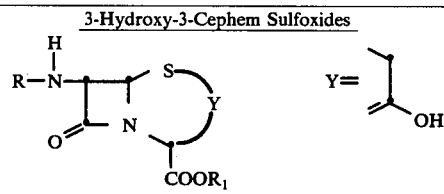

| R | $R_1$ |
|---|---|
| acetyl | diphenylmethyl |
| " | 4-nitrobenzyl |
| " | 4-methoxybenzyl |
| " | 2,2,2-trichloroethyl |
| phenoxyacetyl | benzyl |
| " | diphenylmethyl |
| " | 4-nitrobenzyl |
| " | 4-methoxybenzyl |
| " | 2,2,2-trichloroethyl |
| " | phenacyl |
| phenylacetyl | " |
| " | benzyl |
| " | 4-nitrobenzyl |
| " | 4-methoxybenzyl |
| " | 2,2,2-trichloroethyl |
| H (7-amino) | " |
| " | diphenylmethyl |
| " | 4-nitrobenzyl |
| " | 4-methoxybenzyl |
| " | benzyl |

Especially preferred cephalosporin sulfoxides of this invention are 7-phenoxyacetamido-3-exomethylenecepham-4-carboxylic acid sulfoxide, 7-phenoxyacetamido-3-hydroxy-3-cephem-4-carboxylic acid sulfoxide, 7-phenylacetamido-3-exomethylenecepham-4-carboxylic acid sulfoxide, 7-phenylacetamido-3-hydroxy-3-cephem-4-carboxylic acid sulfoxide, and the benzyl, diphenylmethyl, 4-nitrobenzyl, 4-methoxybenzyl, 2,2,2-trichloroethyl, and phenacyl esters thereof.

The 7-acylamido (or 7-amino)-3-exomethylenecepham-4-carboxylic acid or ester sulfoxides and the 7-acylamido (or 7-amino)-3-hydroxy-3-cephem-4-carboxylic acid ester sulfoxides are useful intermediates in the preparation of cephalosporin antibiotic compounds. For example, the exomethylene sulfoxide in the form of an ester can be isomerized to a 3-methyl-3-cephem ester sulfoxide according to the method disclosed in my copending application Ser. No. 118,941 filed Feb. 25, 1971. According to this method, the 3-exomethylenecepham ester is commingled with an aprotic solvent having a high dielectric constant and a tertiary amine having a pKa of at least 9.5 to effect the isomerization of the exo double bond to the endo position thus providing the desacetoxycephalosporin. For example, diphenylmethyl 7-phenoxyacetamido-3-exomethylenecepham-4-carboxylate sulfoxide is dissolved in the aprotic solvent, dimethylacetamide, and trimethylamine is added to the solution at room temperature with stirring. The isomerization mixture is allowed to stand or is stirred for about 8 to 12 hours. The reaction mixture is then poured into a mixture of water and ethyl acetate and immediately acidified to pH 2 with dilute hydrochloric acid. The ethyl acetate is separated and is washed with dilute hydrochloric acid and with water. The washed solution is then dried over a drying agent such as magnesium sulfate or sodium sulfate and is then evaporated to dryness in vacuo to yield diphenylmethyl 7-phenoxyacetamido-3-methyl-3-cephem-4-carboxylate sulfoxide.

The 3-methyl-3-cephem sulfoxide is then reduced to the sulfide according to the sulfoxide reduction procedure disclosed in U.S. Pat. No. 3,641,041 issued Feb. 8, 1972. For example, the above diphenylmethyl 7-phenoxyacetamido-3-methyl-3-cephem-4-carboxylate sulfoxide is dissolved in N,N-dimethylformamide. One of the disclosed reducing agents for example sodium dithionite or phosphorus trichloride is added and the resulting suspension is stirred at 0° C. while acetyl chloride is added. The cooled reduction suspension is stirred for about one hour and is diluted with water. The organic material of the reaction mixture is extracted with an organic solvent such as ethyl acetate and the extract is washed and dried. The extract is then evaporated under reduced pressure to dryness to yield diphenylmethyl 7-phenoxyacetamido-3-methyl-3-cephem-4-carboxylate.

The foregoing isomerization and sulfoxide reduction reactions are illustrated in the following reaction scheme 4.

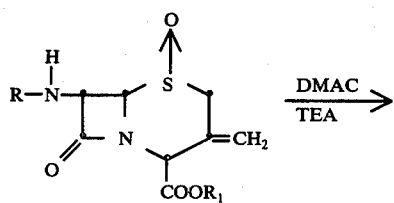

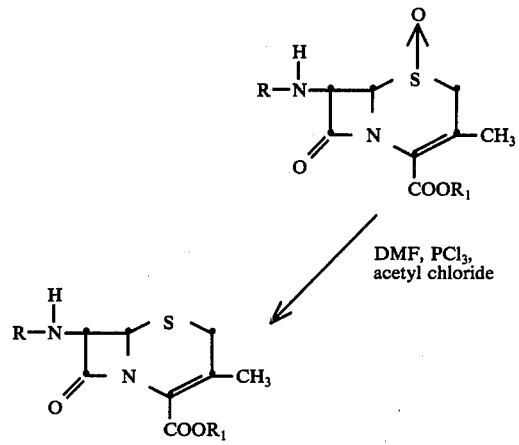

DMAC = dimethylacetamide
TEA = triethylamine
DMF = dimethylformamide

The 7-acylamido (or 7-amino)-3-hydroxy-3-cephem-4-carboxylic acid ester sulfoxides of this invention can be reduced at a temperature of about 5° C. with phosphorus trichloride and acetyl chloride in DMF to provide the corresponding 3-hydroxy-3-cephem ester as the sulfide. The reduction is carried out as described above, however, the temperature is maintained below about 10° C.

The 3-hydroxy-3-cephem ester can then be converted to a 3-alkoxy-3-cephem ester or to a 3-halo-3-cephem ester. For example, 4-nitrobenzyl 7-phenoxyacetamido-3-hydroxy-3-cephem-4-carboxylate is allowed to react in an inert solvent with diazomethane to form 4-nitrobenzyl 7-phenoxyacetamido-3-methoxy-3-cephem-4-carboxylate. The 4-nitrobenzyl group is removed by catalytic hydrogenolysis over palladium on carbon catalyst to provide the antibiotic compound 7-phenoxyacetamido-3-methoxy-3-cephem-4-carboxylic acid. These 3-methoxy-3-cephem compounds are highly active antibiotics and are fully disclosed in my copending applications Ser. Nos. 310,190 and 310,191, filed Nov. 28. 1972 now U.S. Pat. Nos. 3,917,588 and 3,917,587, respectively, both issued Nov. 4, 1975.

Alternatively, the 3-hydroxy-3-cephem esters prepared via the reduction of a sulfoxide compound of the formula I can be reacted with phosphorus trichloride is DMF to effect chlorination of the 3-hydroxy group and provide a 3-chloro-3-cephem ester. For example, 4-nitrobenzyl 7-[2-(2-thienyl)acetamido]-3-hydroxy-3-cephem-4-carboxylate is reacted with phosphorus trichloride in DMF to yield 4-nitrobenzyl 7-[2-(2-thienyl)acetamido]-3-chloro-3-cephem-4-carboxylate. Cleavage of the 4-nitrobenzyl ester group provides the antibiotic compound 7-[2-(2-thienyl)acetamido]-3-chloro-3-cephem-4-carboxylic acid. These 3-halo-3-cephem antibiotics are likewise fully disclosed in my copending applications Ser. Nos. 457,150 and 457,153 filed Apr. 1, 1974 the latter now U.S. Pat. No. 3,925,372 issued Dec. 9, 1975.

The foregoing reactions are illustrated in the following reaction scheme 5.

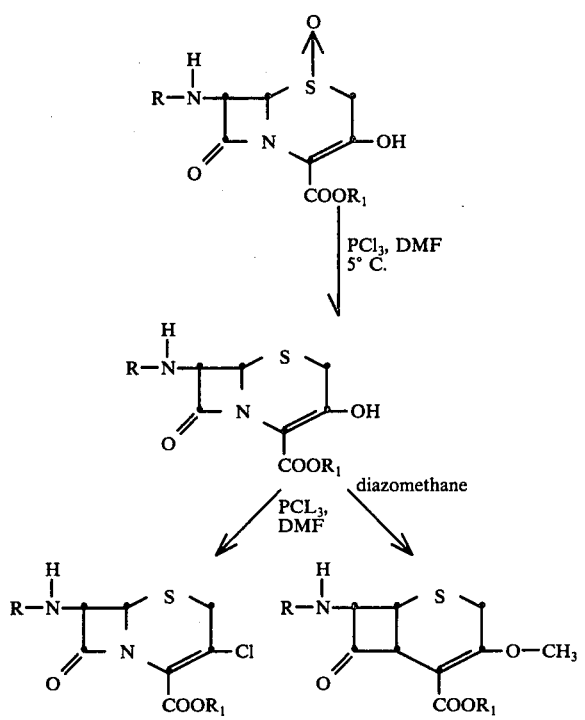

The following examples are provided to further illustrate the present invention.

EXAMPLE 1

A suspension of 340 mg. (1 mmole) of 7-[2-(2-thienyl)-acetamido]-3-exomethylenecepham-4-carboxylic acid in 30 ml. of water was treated with 0.1 N sodium hydroxide to pH 5.7 to form a solution. To the solution were added 120 mg. (1 mmole) of sodium meta periodate and the reaction mixture was stirred at room temperature for 2 hours. The mixture was layered with ethyl acetate and the pH adjusted to 2.5. The ethyl acetate layer was separated and 250 mg. (35% yield) of 7-[2-(2-thienyl)acetamido]-3-exomethylene-cepham-4-carboxylic acid sulfoxide crystallized from the extract before drying. The product melted with decomposition at about 184° C.

Elemental analysis of the sulfoxide product calculated for $C_{14}H_{14}N_2O_5S_2 \cdot 1/2\ H_2O$:

Theory: C, 46.28; H, 4.16; N, 7.71
Found: C, 46.19; H, 4.14; N, 7.58.

NMR (DMSO d$_6$) signals at 6.18 (s, 4H, C$_2$H$_2$ and sidechain CH$_2$), 5.00 (d, 1H, C$_6$H), 4.87 (s, 1H, C$_4$H), 4.68 and 4.36 (2s, 2H, C$_3$, CH$_2$), 4.39 (q, 1H, C$_7$H), 3.10–2.60 (m, 3H, aromatic H) and 1.94 (d, 1H, amide NH) tau.

EXAMPLE 2

2',2',2'-Trichloroethyl 7-phenoxyacetamido-3-methylenecephem-4-carboxylate 1-oxide.

A mixture of 4.82 g (10 mmol.) of 2',2',2'-trichloroethyl 6-phenoxyacetamidopenicillanate 1-oxide, 150 ml. of dry toluene, and 2.0 g. (11 mmol.) of N-chlorophthalimide was refluxed for 60 minutes using a Dean-Stark adapter. A 5 ml. aliquot of mixture was evaporated; the nmr spectrum thereof showed a complete conversion to the expected sulfinyl chloride.

The solution of the sulfinyl chloride in toluene was cooled to ca. 40°, and 1.4 ml. of stannic chloride was added. The mixture was stirred for 60 minutes and then was washed successively with 1N.HCl, aqueous NaHCO$_3$, and brine and dried (MgSO$_4$). After evaporation of the solvent, 30 ml. of chloroform was added to the residue, and the insoluble phthalimide was filtered. The filtrate was evaporated to dryness and the yellow amorphous product was dried in vacuo. Yield: 3.4 g. (70 percent) of the title compound; nmr (CDCl$_3$) 3.56 and 3.80 (ABq, 2, J=14 Hz), 4.48 (s,2), 4.75 (m, 2, CH$_2$CCl$_3$), 4.89 (d, 1, J=4.5 Hz), 5.33 (s, 1), 5.48 (s, 1), 5.78 (s, 1), 5.9 and 6.07 (q, 1, J=4.5 Hz), 6.8–7.4 (m, 5, ArH), and 8.1 (d, NH, J=10 Hz).

EXAMPLE 3

2',2',2'-Trichloroethyl 7-phenylacetamido-3-methylenecepham-4-carboxylate 1-oxide A mixture of 1.0 g. of 2',2',2'-trichloroethyl 7-phenylacetamidopenicillanate 1-oxide, 0.5 g. of N-chlorosuccinimide and 80 ml. of dry toluene was refluxed for 90 minutes, then cooled, and washed (water and brine). To the resulting solution of sulfinyl chloride was added 0.28 ml. of anhydrous stannic chloride. The resulting mixture was stirred for 90 minutes. After washing (water and brine) the solvent was evaporated in vacuo to dryness. The product crystallized from ethyl acetate-ether to provide the title product as colorless prisms: m.p. 187°–189°; nmr (CDCl$_3$) δ3.5 and 3.81 (ABq, 2, J=14 Hz); 3.63 (s, 2), 4.8 (m, 2), 4.9 (d, 1, J=4.5 Hz), 5.37 (s, 1), 5.5 (s, 1), 5.82 (s, 1), 5.9 and 6.07 (q, 1, J=4.5 Hz and 10.0 Hz), 7.0 (d, NH, J=10 Hz), 7.33 (s, 5).

I claim:
1. The compound of the formula

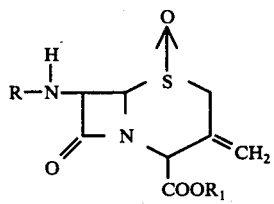

wherein R is phenoxyacetyl or phenylacetyl and R$_1$ is hydrogen, p-nitrobenzyl, p-methoxybenzyl, benzhydryl, or 2,2,2-trichloroethyl.

2. The compound of claim 1, said compound being p-nitrobenzyl 7-phenoxyacetamido-3-exomethylenecepham-4-carboxylate sulfoxide.

3. The compound of claim 1, said compound being 7-phenoxyacetamido-3-exomethylenecepham-4-carboxylic acid sulfoxide.

4. The compound of claim 1, said compound being p-nitrobenzyl 7-phenylacetamido-3-exomethylenecepham-4-carboxylate sulfoxide.

5. The compound of claim 1, said compound being 7-phenylacetamido-3-exomethylenecepham-4-carboxylic acid sulfoxide.

* * * * *

Notice of Adverse Decision in Interference

In Interference No. 100,023, involving Patent No. 4,060,688, R. R. Chauvette, CEPHALOSPORIN INTERMEDIATES, final judgment adverse to the patentee was rendered Mar. 31, 1980, as to claims 1–5.

[*Official Gazette June 10, 1980.*]